United States Patent
Tang et al.

[11] Patent Number: 5,609,996
[45] Date of Patent: Mar. 11, 1997

[54] PHOTOGRAPHIC EMULSION LAYER CONTAINING PYRAZOLOAZOLE COUPLER EXHIBITING IMPROVED DYE LIGHT FADE

[75] Inventors: Ping W. Tang; Stanley W. Cowan; David J. Decker; Terrence C. Mungal, all of Rochester, N.Y.

[73] Assignee: Eastman Kodak Company, Rochester, N.Y.

[21] Appl. No.: 608,916

[22] Filed: Feb. 29, 1996

[51] Int. Cl.$^6$ .................................. G03C 7/38
[52] U.S. Cl. ................ 430/386; 430/387; 430/558
[58] Field of Search ............... 430/386, 387, 430/558

[56] References Cited

FOREIGN PATENT DOCUMENTS

| | | | |
|---|---|---|---|
| 0704758 | 3/1996 | European Pat. Off. | 430/558 |
| 8-146575 | 6/1996 | Japan | 430/558 |

*Primary Examiner*—Lee C. Wright
*Attorney, Agent, or Firm*—Arthur E. Kluegel

[57] ABSTRACT

A photographic light sensitive silver halide emulsion layer has associated therewith a pyrazoloazole dye-forming coupler having the formula:

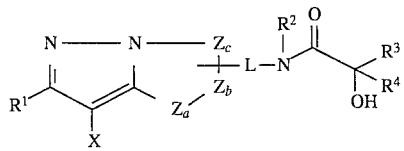

wherein:

$R^1$ is a substituent bonded to the pyrazolotriazole nucleus by a fully substituted carbon atom;

X is hydrogen or a coupling-off group;

L is a divalent linking group;

$R^2$, $R^3$, and $R^4$ are independently hydrogen or substituent groups; and $Z_a$, $Z_b$, and $Z_c$ are independently —C(R')(R")—, =N—, =C(R')—, or —NH—, wherein R', and R" are independently H or a substituent, provided that one of either the $Z_a$—$Z_b$ or the $Z_b$—$Z_c$ bond is a double bond and the other is a single bond, and provided that when the $Z_b$—$Z_c$ bond is a double bond, it may form part of a fused ring.

22 Claims, No Drawings

PHOTOGRAPHIC EMULSION LAYER CONTAINING PYRAZOLOAZOLE COUPLER EXHIBITING IMPROVED DYE LIGHT FADE

FIELD OF THE INVENTION

This invention relates to a photographic silver halide emulsion layer having associated therewith a dye-forming pyrazoloazole coupler having an alpha hydroxycarboxamide substituent.

BACKGROUND OF THE INVENTION

Silver halide photography depends on the formation of dyes in order to reproduce an image. These dyes are typically formed from couplers present in or adjacent to the light sensitive silver halide emulsion layers which react to image light upon exposure. During development, the latent image recorded by the silver halide emulsion is developed to amplify the image. During this process in which silver halide is reduced to elemental silver, the color developer compound used is at the same time oxidized, as is typical in a redox reaction. The oxidized developer then reacts or couples with the coupler compound present in or adjacent to the emulsion layer to form a dye of the desired color.

Typically, a silver halide emulsion layer containing a magenta dye-forming coupler is sensitized to green light. This facilitates so-called negative-positive processing in which the image is initially captured in a negative format where black is captured as white, white as black, and the colors as there complimentary color (e.g. green as magenta; blue as yellow; and red as cyan). Then the initial image can be optically printed in the correct colors on a reflective background through the device of optical printing which has the effect of producing a negative of the negative or a positive of the image.

Viewable images may also be produced through reversal processing in which the initial negative image is reversed by using a black and white developer, processed to remove the developed silver, and by then fogging the element in the presence of color developer to provide developed silver in proportion to the amount of image light with corresponding dye formation.

One of the difficulties with color couplers is achieving both a desirable dye forming activity and a satisfactory dye light stability. In other words, it is necessary for the coupler to be capable of forming sufficient dye density during the development time of the process (e.g. 90 seconds). It is also desirable that the dye formed by reaction between the oxidized color developer and the coupler exhibit a degree of stability against light degradation which is satisfactory for the type of exposure which the photographic element will be exposed.

Couplers that form magenta dyes upon reaction with oxidized color developing agent are described in such representative patents and publications as: U.S. Pat. Nos. 2,311,082, 2,343,703, 2,369,489, 2,600,788, 2,908,573, 3,062,653, 3,152,896, 3,519,429, 3,758,309, 4,540,654, and "Farbkupplereine Literature Ubersicht," published in Agfa Mitteilungen, Band III, pp. 126–156 (1961). Typically, such couplers are pyrazotones, pyrazolotriazoles, or pyrazolobenzimidazoles that form magenta dyes upon reaction with oxidized color developing agents. The present invention is concerned with the pyrazoloazole type of dye-forming coupler. There have been disclosed both magenta and cyan dye forming versions of these couplers. In particular, the couplers of the invention include a 1H-pyrazolo[1,5-b][1,2,4] and a 1H-pyrazolo[3,2-c][1,2,4]triazole compound. Such couplers have been found advantageous because the dyes formed from such couplers provide improved spectral absorption curves and therefore give better color rendition. Dye light stability would be required for either magenta or cyan dye forming couplers.

In a series of published Japanese patent applications, J05-273715; J05-323531; J05-323532; J05-323533; J05-323534; and J05-323538; various suggestions are presented for suitable 3-position substituents for pyrazoloazole compounds. Among the suggestions are amine or amide substituents bonded to a carbon alpha to the 3-position of the pyrazolotriazole nucleus. None of the proposed couplers is adequate.

It is therefore a problem to be solved to provide photographic silver halide emulsion layer which will exhibit the desired dye forming ability and will also enable the formation of a dye which has improved light stability.

SUMMARY OF THE INVENTION

A photographic light sensitive silver halide emulsion layer has associated therewith a pyrazoloazole dye-forming coupler having the formula:

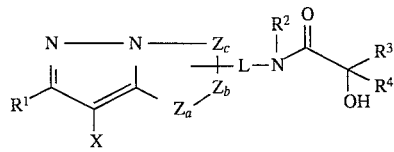

wherein:

$R^1$ is a substituent bonded to the pyrazolotriazole nucleus by a fully substituted carbon atom;

X is hydrogen or a coupling-off group;

L is a divalent linking group;

$R^2$, $R^3$, and $R^4$ are independently hydrogen or substituent groups; and $Z_a$, $Z_b$, and $Z_c$ are independently —C(R")(R")—, =N—, =C(R')—, or —NH—, wherein R', and R" are independently H or a substituent, provided that one of either the $Z_a$—$Z_b$ or the $Z_b$—$Z_c$ bond is a double bond and the other is a single bond, and provided that when the $Z_b$—$Z_c$ bond is a double bond, it may form part of a fused ring.

The invention also comprises a dye-forming coupler compound, a photographic element containing the coupler compound, and a process for forming an image in the photographic element of the invention.

The invention provides photographic materials which exhibit an improved resistance to fading of the formed dye upon exposure to light.

DETAILED DESCRIPTION OF THE INVENTION

As described for the coupler of the invention, $R^1$ is a substituent bonded to the pyrazoloazole nucleus by a fully substituted carbon atom. Suitable preferred examples include tricyclohexylmethyl and tertiary carbon groups containing from 4 to 8 carbon atoms with t-butyl, t-pentyl, triethylmethyl, and methyldiethylmethyl being preferred.

X is hydrogen or a coupling-off group. Any known coupling-off group can be employed. Such groups are described more fully hereafter and include aryloxy, arylthio, halogen, and heterocyclic groups such as nitrogen heterocycles. Typically with this kind of coupler, a halogen such as chloride or a heterocyclic group such as

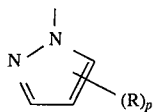

where each R is an independently selected substituent and p is 0 to 3 are particularly suitable.

$R^2$, $R^3$, and $R^4$ are independently hydrogen or substituent groups. The identity of these groups is not believed to play a significant role in the advantages of the invention so their selection may be made from a broad list. $R^4$ is preferably an alkyl, aryl, alkoxy, or aryloxy group. $R^2$ and $R^3$ are preferably selected from hydrogen or the groups from which R4 may be selected. These groups are typically alkyl or alkoxy groups of 16 or less carbon atoms or aryl or aryloxy groups of less than 32 carbon atoms. Particularly suitable are alkyl groups having up to 12 carbon atoms, such as methyl, butyl, cyclohexyl, and dodecyl.

L is any divalent linking group such as an arylene or alkylene group. The group may be unsubstituted such as propyl, butyl, cyclohexyl or dodecyl or may be substituted or may be interrupted in its main chain to the carboxamide group by one or more oxygen atoms such as —$(CH_2)_3OC_{12}H_{24}$—, —$(OCH_2)_3OCH_2$—, —$CH_2CH_2OCH_2CH_2OCH_3$—, —$(CH_2)_3OCH_2CH_2OCH_2CH_2OCH_2$—, —$(CH_2)_3$—O—$C_6H_4$—, or —$(CH_2)_2$—O—$C_6H_4$—.

The couplers of the invention may be prepared in accordance with the following general scheme:

The Z groups are as defined in the summary of the invention. Specifically suitable embodiments are where $Z_a$ is —NH—, $Z_b$ is =N—, and $Z_c$ is =C(R')— and where $Z_a$ is —NH—, $Z_b$ is =C(R')—, and $Z_c$ is =N—.

The following couplers exemplify those useful in the invention:

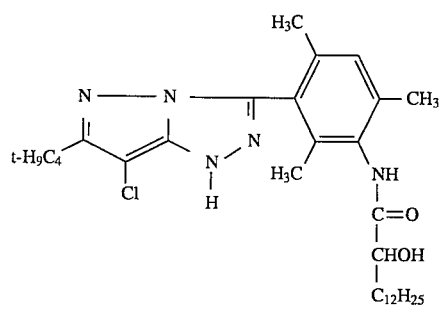

M-1

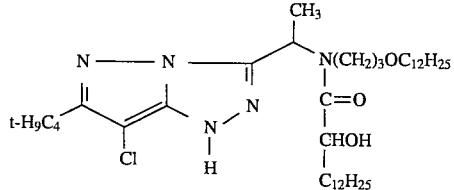

M-2

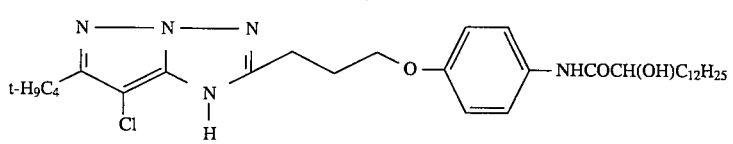

M-3

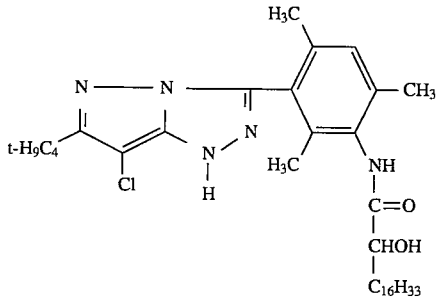

M-4

-continued
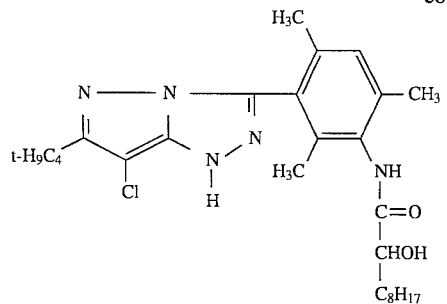 M-5
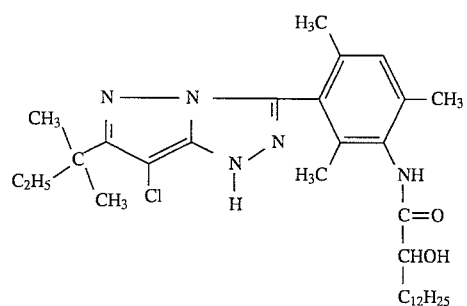 M-6
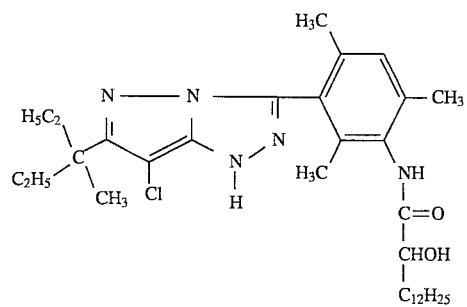 M-7
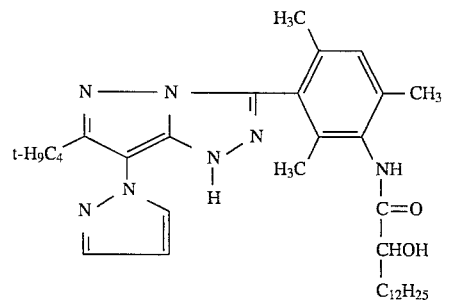 M-8
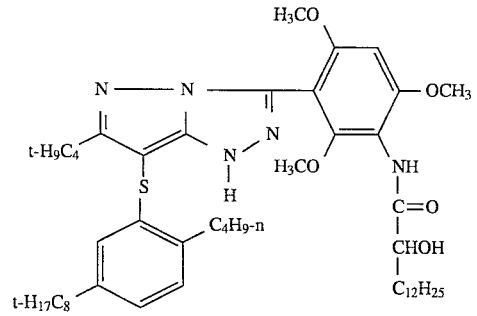 M-9

M-10
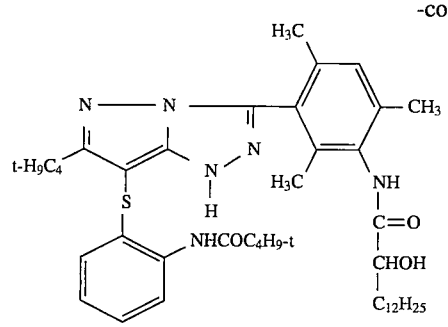
M-11
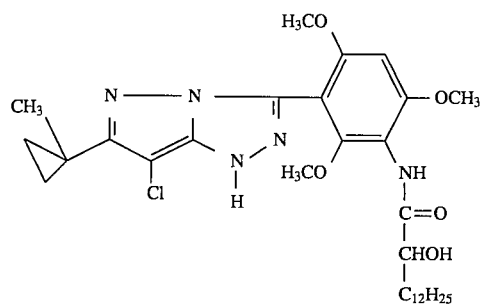
M-12
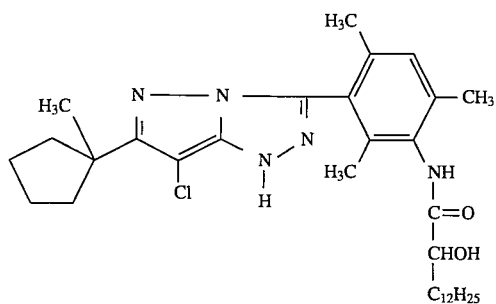
M-13
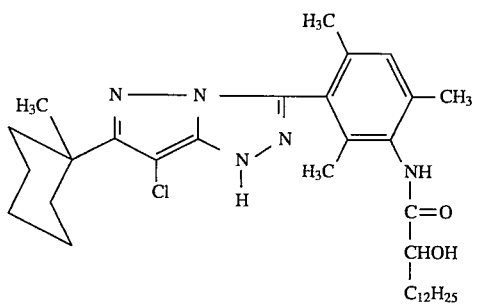
M-14
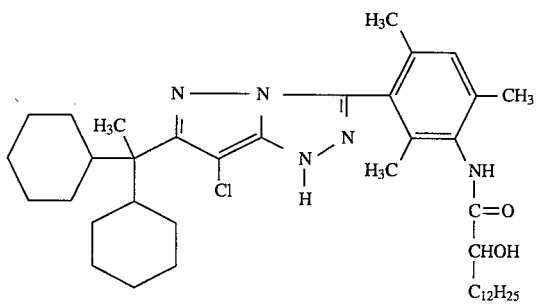
M-15
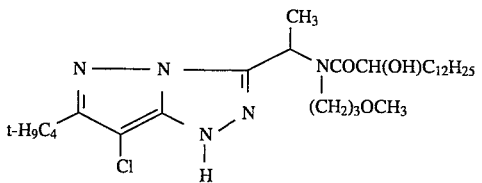

-continued
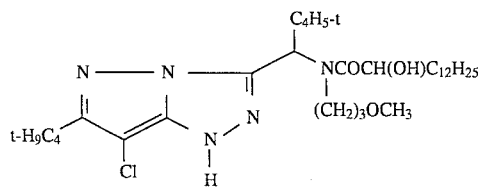
M-16
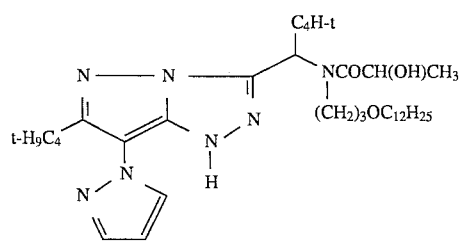
M-17
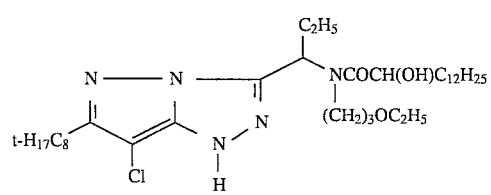
M-18
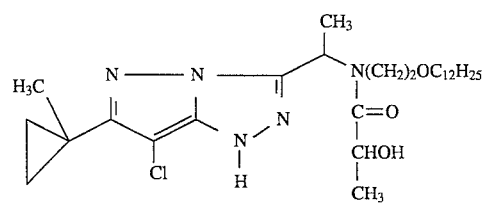
M-19
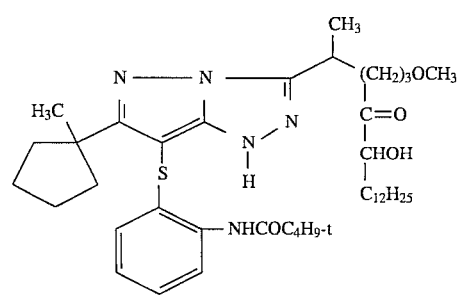
M-20
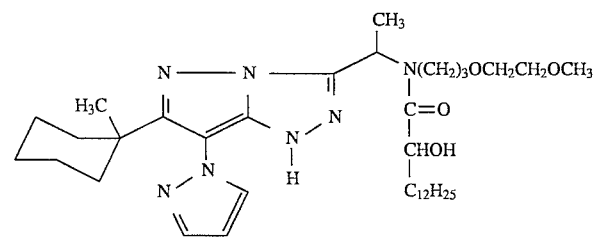
M-21
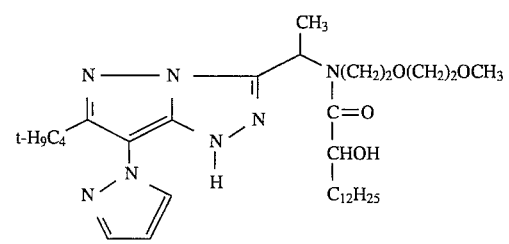
M-22

-continued
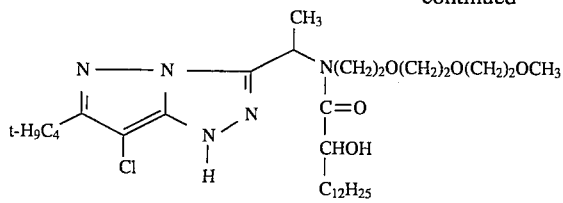
M-23
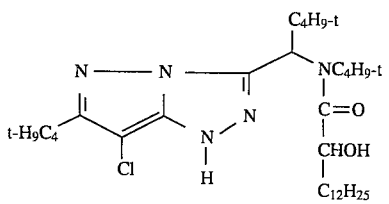
M-24
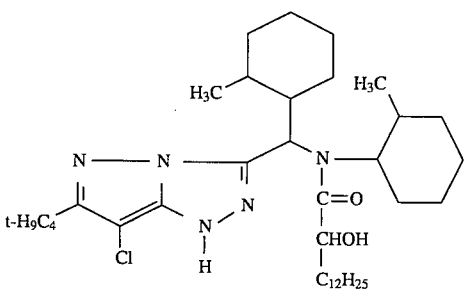
M-25
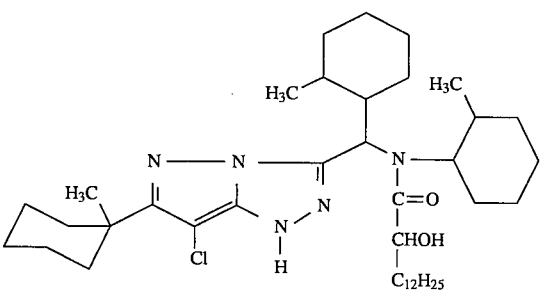
M-26
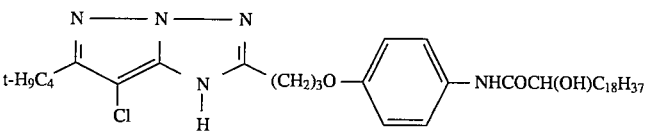
M-27
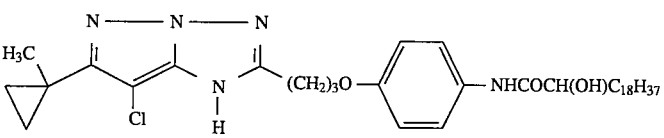
M-28
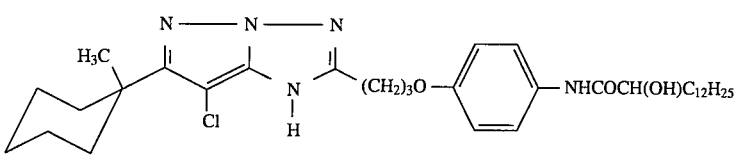
M-29
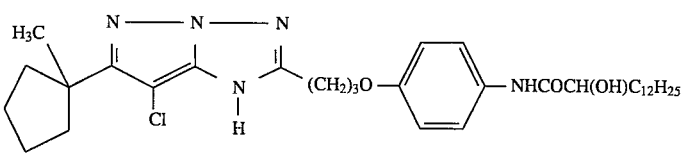
M-30

-continued
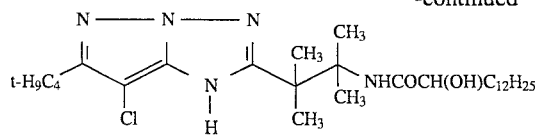  M-31
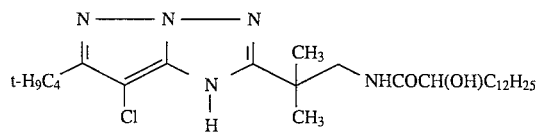  M-32
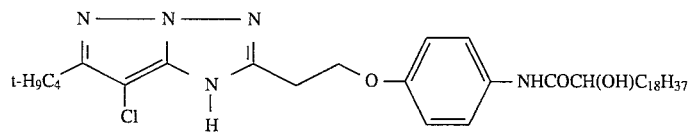  M-33
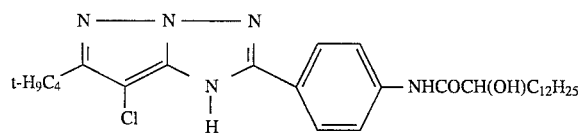  M-34
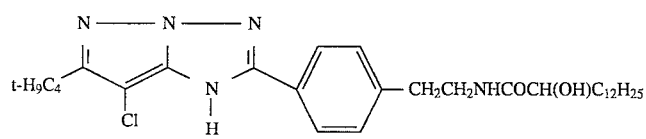  M-35
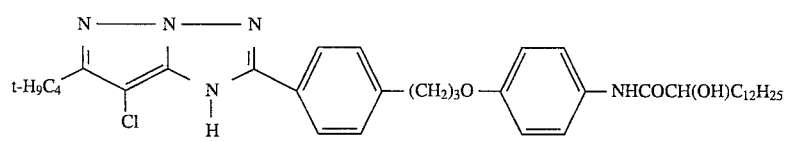  M-36
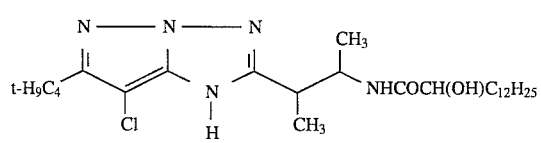  M-37
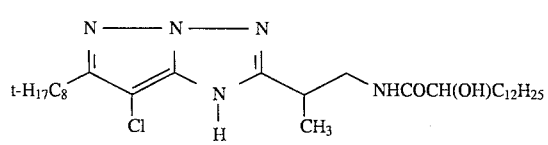  M-38
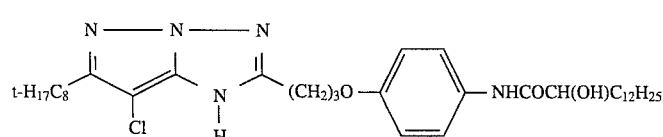  M-39
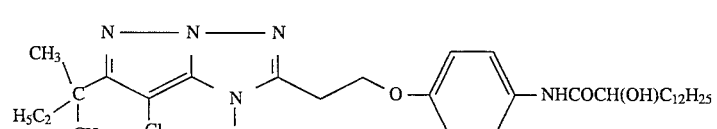  M-40
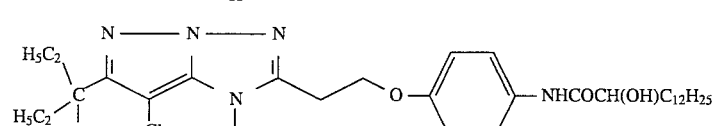  M-41
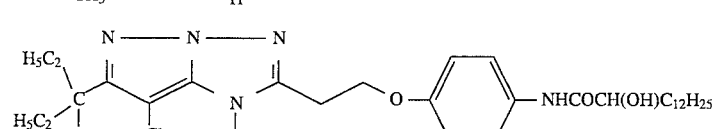  M-42

-continued

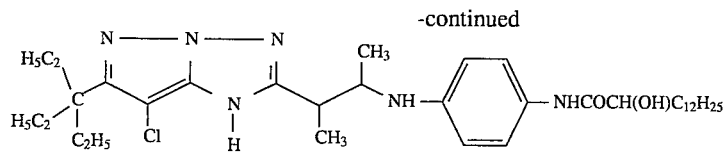

M-43

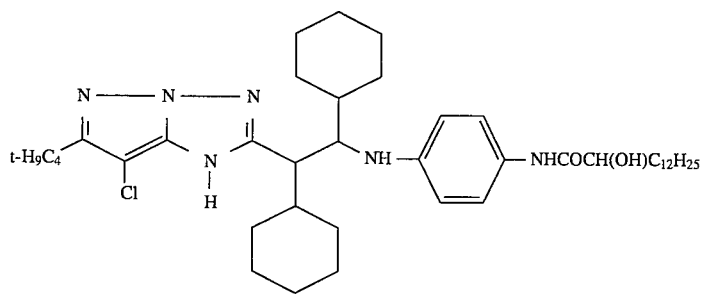

M-44

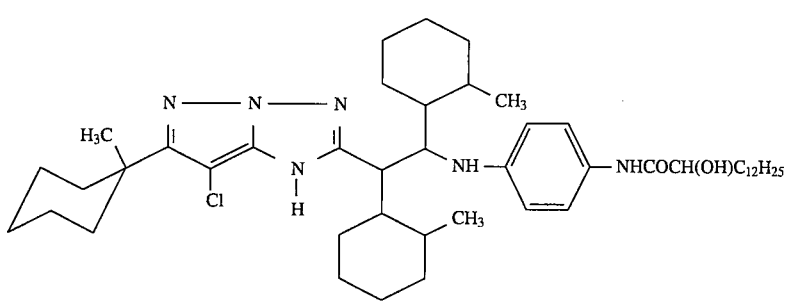

M-45

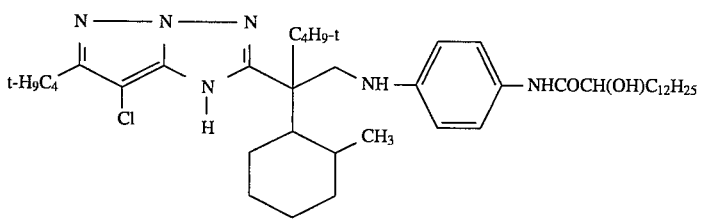

M-46

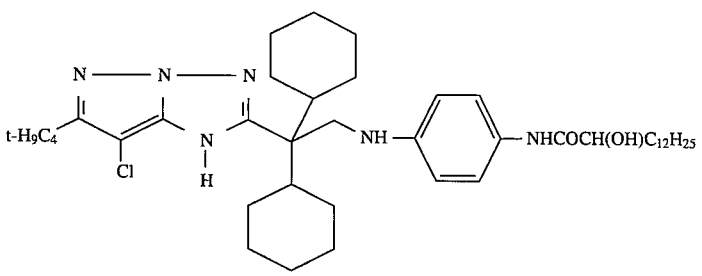

M-47

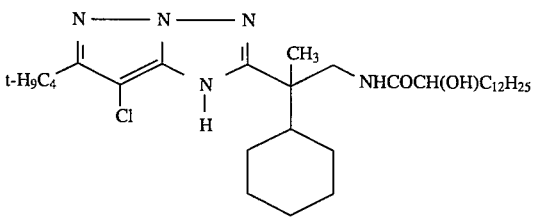

M-48

The invention also provides a coupler compound, a photographic element containing the emulsion layer of the invention, and an imaging process. Couplers of various colors such as magenta and cyan are obtainable from the compounds of the invention by the judicious selection of the coupler substituents. The coupler may be used for other than photographic purposes. The element is a conventional multilayer photographic element of one or more colors as described hereafter. The element may be employed to capture a latent image, and to subsequently form an image through the development of a dye image using a color developer such as a para-phenylene diamine.

Unless otherwise specifically stated, substituent groups which may be substituted on molecules herein include any groups, whether substituted or unsubstituted, which do not destroy properties necessary for photographic utility. When the term "group" is applied to the identification of a substituent containing a substitutable hydrogen, it is intended to encompass not only the substituent's unsubstituted form, but also its form further substituted with any group or groups as herein mentioned. Suitably, the group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain alkyl, such as methyl, trifluoromethyl, ethyl, t-butyl, 3-(2,4-di-t-pentylphenoxy)propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy)butyramido, alpha-(3-pentadecylphenoxy)hexanamido, alpha-(4-hydroxy-3-t-butylphenoxy)tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecylphenylcarbonylamino, p-toluylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-ptoluylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-toluylsulfonamido, p-dodecylbenzenesulfonamido, N-methyltetradecylsulfonamido, N,N-dipropylsulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl] sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-toluylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-toluylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups, etc. Generally, the above groups and substituents thereof may include those having up to 48 carbon atoms, typically 1 to 36 carbon atoms and usually less than 24 carbon atoms, but greater numbers are possible depending on the particular substituents selected.

The materials of the invention can be used in any of the ways and in any of the combinations known in the art. Typically, the invention materials are incorporated in a silver halide emulsion and the emulsion coated as a layer on a support to form part of a photographic element. Alternatively, unless provided otherwise, they can be incorporated at a location adjacent to the silver halide emulsion layer where, during development, they will be in reactive association with development products such as oxidized color developing agent. Thus, as used herein, the term "associated" signifies that the compound is in the silver halide emulsion layer or in an adjacent location where, during processing, it is capable of reacting with silver halide development products.

To control the migration of various components, it may be desirable to include a high molecular weight hydrophobe or "ballast" group in coupler molecules. Representative ballast groups include substituted or unsubstituted alkyl or aryl groups containing 8 to 48 carbon atoms. Representative substituents on such groups include alkyl, aryl, alkoxy, aryloxy, alkylthio, hydroxy, halogen, alkoxycarbonyl, aryloxycarbonyl, carboxy, acyl, acyloxy, amino, anilino, carbonamido, carbamoyl, alkylsulfonyl, arylsulfonyl, sulfonamido, and sulfamoyl groups wherein the substituents typically contain 1 to 42 carbon atoms. Such substituents can also be further substituted.

The photographic elements can be single color elements or multicolor elements. Multicolor elements contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

If desired, the photographic element can be used in conjunction with an applied magnetic layer as described in *Research Disclosure*, November 1992, Item 34390 published by Kenneth Mason Publications, Ltd., Dudley Annex, 12a North Street, Emsworth, Hampshire PO10 7DQ, ENGLAND, and as described in Hatsumi Kyoukai Koukai Gihou No. 94-6023, published Mar. 15, 1994, available from the Japanese Patent Office, the contents of which are incoporated herein by reference. When it is desired to employ the inventive materials in a small format film, *Research Disclosure*, June 1994, Item 36230, provides suitable embodiments.

In the following discussion of suitable materials for use in the emulsions and elements of this invention, reference will be made to *Research Disclosure*, September 1994, Item 36544, available as described above, which will be identified hereafter by the term "Research Disclosure". The contents of the Research Disclosure, including the patents and publications referenced therein, are incorporated herein by reference, and the Sections hereafter referred to are Sections of the Research Disclosure.

Except as provided, the silver halide emulsion containing elements employed in this invention can be either negative-working or positive-working as indicated by the type of processing instructions (i.e. color negative, reversal, or direct positive processing) provided with the element. Suitable emulsions and their preparation as well as methods of chemical and spectral sensitization are described in Sections I through V. Various additives such as UV dyes, brighteners, antifoggants, stabilizers, light absorbing and scattering materials, and physical property modifying addenda such as hardeners, coating aids, plasticizers, lubricants and matting agents are described, for example, in Sections II and VI through VIII. Color materials are described in Sections X through XIII. Scan facilitating is described in Section XIV. Supports, exposure, development systems, and processing methods and agents are described in Sections XV to XX. Certain desirable photographic elements and processing steps, particularly those useful in conjunction with color reflective prints, are described in *Research Disclosure*, Item 37038, February 1995.

Coupling-off groups are well known in the art. Such groups can determine the chemical equivalency of a coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, dye hue adjustment, development acceleration or inhibition, bleach acceleration or inhibition, electron transfer facilitation, color correction and the like.

The presence of hydrogen at the coupling site provides a 4-equivalent coupler, and the presence of another coupling-off group usually provides a 2-equivalent coupler. Representative classes of such coupling-off groups include, for example, chloro, alkoxy, aryloxy, hetero-oxy, sulfonyloxy, acyloxy, acyl, heterocyclyl, sulfonamido, mercaptotetrazole, benzothiazole, mercaptopropionic acid, phosphonyloxy, arylthio, and arylazo. These coupling-off groups are described in the art, for example, in U.S. Pat. Nos. 2,455, 169, 3,227,551, 3,432,521, 3,476,563, 3,617,291, 3,880,661, 4,052,212 and 4,134,766; and in UK. Patents and published application Nos. 1,466,728, 1,531,927, 1,533,039, 2,006, 755A and 2,017,704A, the disclosures of which are incorporated herein by reference.

Image dye-forming couplers may be included in the element such as couplers that form cyan dyes upon reaction with oxidized color developing agents which are described in such representative patents and publications as: U.S. Pat. Nos. 2,367,531, 2,423,730, 2,474,293, 2,772,162, 2,895, 826, 3,002,836, 3,034,892, 3,041,236, 4,333,999, 4,883,746 and "Farbkuppler-eine Literature Ubersicht," published in Agfa Mitteilungen, Band III, pp. 156 –175 (1961). Preferably such couplers are phenols and naphthols that form cyan dyes on reaction with oxidized color developing agent.

Couplers that form yellow dyes upon reaction with oxidized color developing agent are described in such representative patents and publications as: U.S. Pat. Nos. 2,298, 443, 2,407,210, 2,875,057, 3,048,194, 3,265,506, 3,447,928, 4,022,620, 4,443,536, and "Farbkuppler-eine Literature Ubersicht," published in Agfa Mitteilungen, Band III, pp. 112–126 (1961). Such couplers are typically open chain ketomethylene compounds.

Couplers that form colorless products upon reaction with oxidized color developing agent are described in such representative patents as: UK. Patent No. 861,138; U.S. Pat. Nos. 3,632,345, 3,928,041, 3,958,993 and 3,961,959. Typically such couplers are cyclic carbonyl containing compounds that form colorless products on reaction with an oxidized color developing agent.

Couplers that form black dyes upon reaction with oxidized color developing agent are described in such representative patents as U.S. Pat. Nos. 1,939,231; 2,181,944; 2,333,106; and 4,126,461; German OLS No. 2,644,194 and German OLS No. 2,650,764. Typically, such couplers are resorcinols or m-aminophenols that form black or neutral products on reaction with oxidized color developing agent.

In addition to the foregoing, so-called "universal" or "washout" couplers may be employed. These couplers do not contribute to image dye-formation. Thus, for example, a naphthol having an unsubstituted carbamoyl or one substituted with a low molecular weight substituent at the 2- or 3-position may be employed. Couplers of this type are described, for example, in U.S. Pat. Nos. 5,026,628, 5,151, 343, and 5,234,800.

It may be useful to use a combination of couplers any of which may contain known ballasts or coupling-off groups such as those described in U.S. Pat. Nos. 4,301,235; 4,853, 319 and 4,351,897. The coupler may contain solubilizing groups such as described in U.S. Pat. No. 4,482,629. The coupler may also be used in association with "wrong" colored couplers (e.g. to adjust levels of interlayer correction) and, in color negative applications, with masking couplers such as those described in EP 213.490; Japanese Published Application 58-172,647; U.S. Pat. Nos. 2,983, 608; 4,070,191; and 4,273,861; German Applications DE 2,706,117 and DE 2,643,965; UK. Patent 1,530,272; and Japanese Application 58-113935. The masking couplers may be shifted or blocked, if desired.

The invention materials may be used in association with materials that accelerate or otherwise modify the processing steps e.g. of bleaching or fixing to improve the quality of the image. Bleach accelerator releasing couplers such as those described in EP 193,389; EP 301,477; U.S. Pat. Nos. 4,163, 669; 4,865,956; and 4,923,784, may be useful. Also contemplated is use of the compositions in association with nucleating agents, development accelerators or their precursors (UK Patent 2,097,140; UK. Patent 2,131,188); electron transfer agents (U.S. Pat. Nos. 4,859,578; 4,912,025); anti-fogging and anti color-mixing agents such as derivatives of hydroquinones, aminophenols, amines, gallic acid; catechol; ascorbic acid; hydrazides; sulfonamidophenols; and non color-forming couplers.

The invention materials may also be used in combination with filter dye layers comprising colloidal silver sol or yellow, cyan, and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. Nos. 4,420,556; and 4,543,323.) Also, the compositions may be blocked or coated in protected form as described, for example, in Japanese Application 61/258,249 or U.S. Pat. No. 5,019,492.

The invention materials may further be used in combination with image-modifying compounds such as "Developer Inhibitor-Releasing" compounds (DIR's). DIR's useful in conjunction with the compositions of the invention are known in the art and examples are described in U.S. Patent Nos. 3,137,578; 3,148,022; 3,148,062; 3,227,554; 3,384,657; 3,379,529; 3,615,506; 3,617,291; 3,620,746; 3,701,783; 3,733,201; 4,049,455; 4,095,984; 4,126,459; 4,149,886; 4,150,228; 4,211,562; 4,248,962; 4,259,437; 4,362,878; 4,409,323; 4,477,563; 4,782,012; 4,962,018; 4,500,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319 ; 336,411; 346, 899; 362, 870; 365,252; 365,346; 373,382 ; 376,212; 377,463; 378,236; 384,670; 396,486; 401,612; 401,613.

Such compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference. Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazoles. In a preferred embodiment, the inhibitor moiety or group is selected from the following formulas:

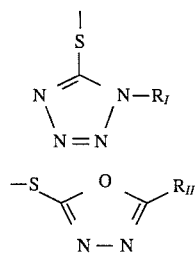

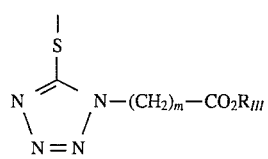

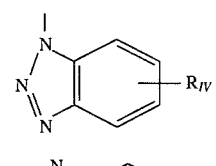

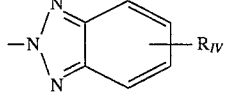

wherein $R_I$ is selected from the group consisting of straight and branched alkyls of from 1 to about 8 carbon atoms, benzyl, phenyl, and alkoxy groups and such groups containing none, one or more than one such substituent; $R_{II}$ is selected from $R_I$ and —$SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, —$COOR_V$ and —$NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

As mentioned, the developer inhibitor-releasing coupler may include a timing group, which produces the time-delayed release of the inhibitor group such as groups utilizing the cleavage reaction of a hemiacetal (U.S. Pat. No. 4,146,396, Japanese Applications 60-249148; 60-249149); groups using an intramolecular nucleophilic substitution reaction (U.S. Pat. No. 4,248,962); groups utilizing an electron transfer reaction along a conjugated system (U.S. Pat. Nos. 4,409,323; 4,421,845; Japanese Applications 57-188035; 58-98728; 58-209736; 58-209738) groups utilizing ester hydrolysis (German Patent Application (OLS) No. 2,626,315); groups utilizing the cleavage of imino ketals (U.S. Pat. No. 4,546,073); groups that function as a coupler or reducing agent after the coupler reaction (U.S. Pat. Nos. 4,438,193; 4,618,571) and groups that combine the features describe above. It is typical that the timing group or moiety is of one of the formulas:

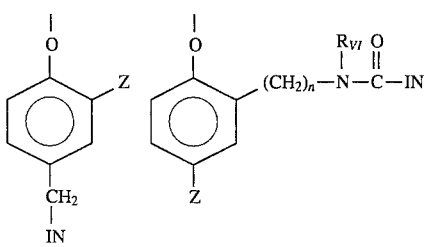

wherein IN is the inhibitor moiety, Z is selected from the group consisting of nitro, cyano, alkylsulfonyl; sulfamoyl (—$SO_2NR_2$); and sulfonamido (—$NRSO_2R$) groups; n is 0 or 1; and $R_{VI}$ is selected from the group consisting of substituted and unsubstituted alkyl and phenyl groups. The oxygen atom of each timing group is bonded to the coupling-off position of the respective coupler moiety of the DIAR.

Suitable developer inhibitor-releasing couplers for use in the present invention include, but are not limited to, the following:

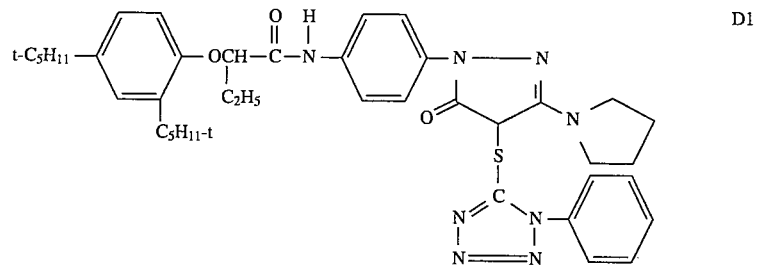
D1

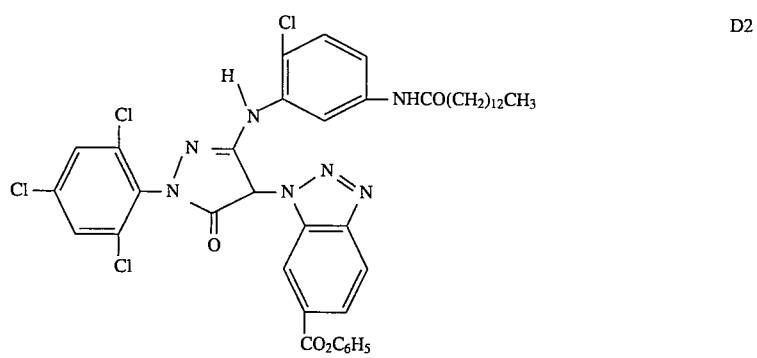
D2

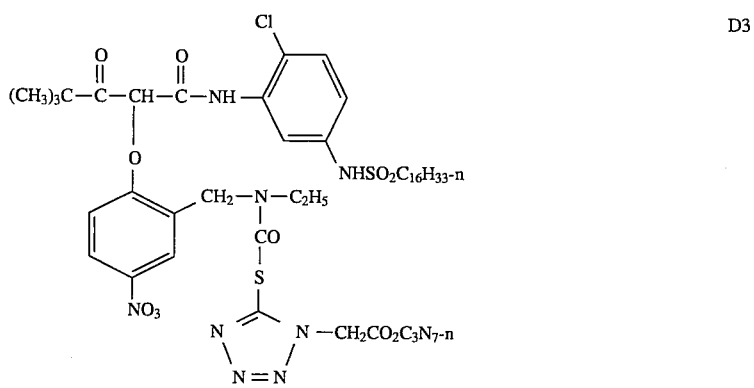
D3

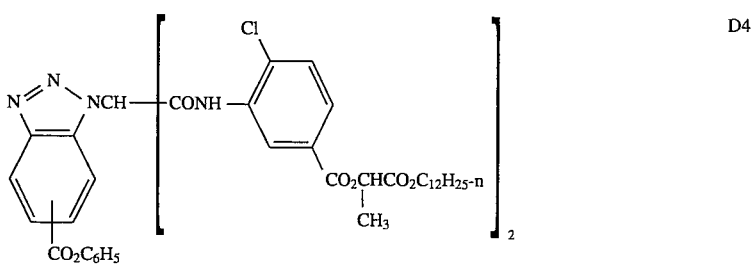
D4

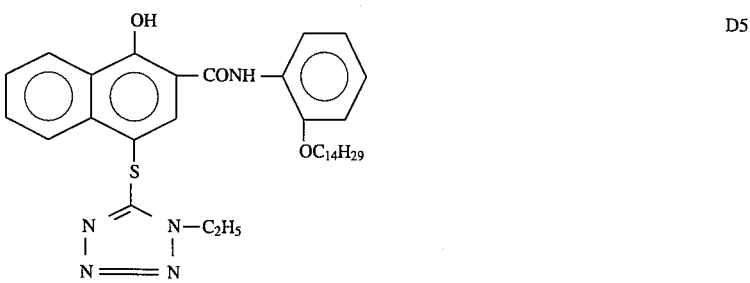
D5

D6
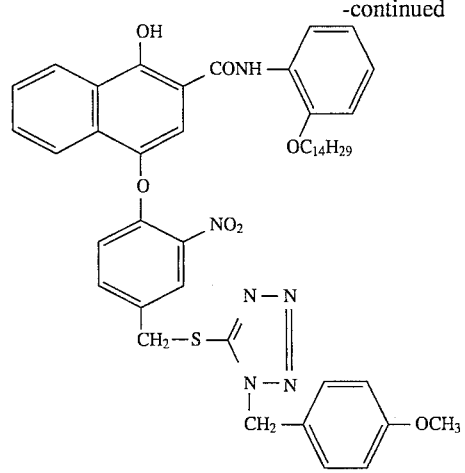
D7
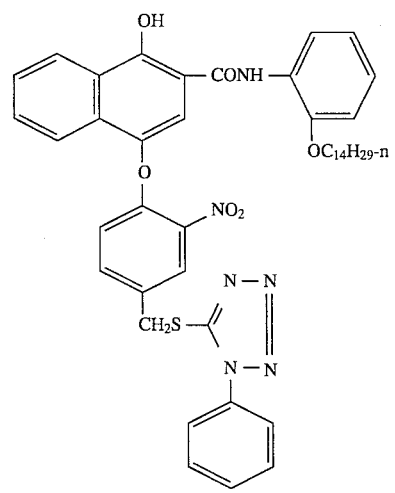
D8
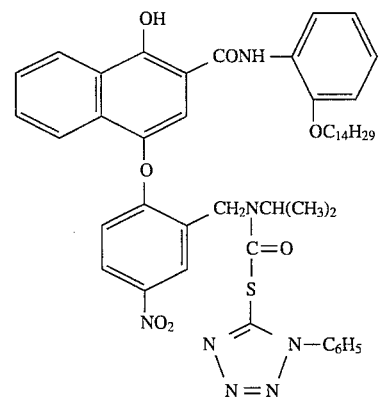

D9

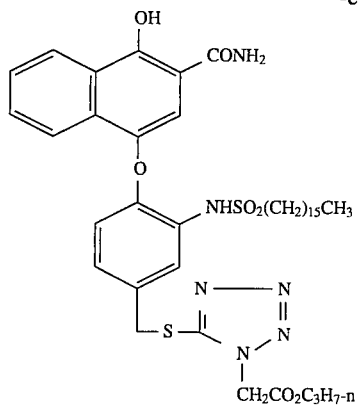

D10

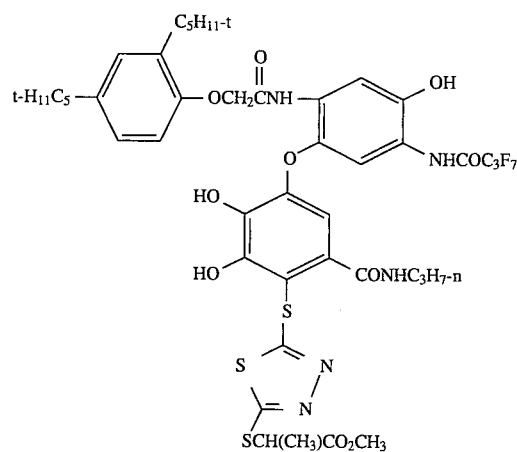

D-11

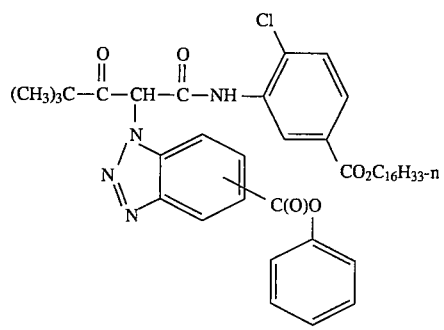

D-12

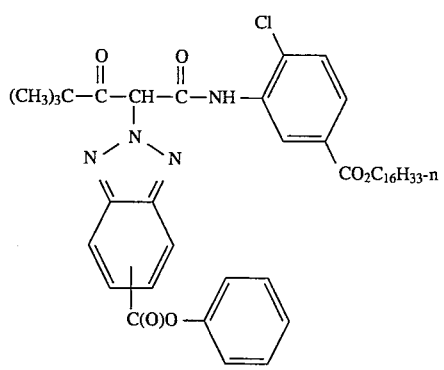

It is also contemplated that the concepts of the present invention may be employed to obtain reflection color prints as described in *Research Disclosure*, November 1979, Item 18716, available from Kenneth Mason Publications, Ltd, Dudley Annex, 12a North Street, Emsworth, Hampshire P0101 7DQ, England, incorporated herein by reference. Materials of the invention may be coated on pH adjusted support as described in U.S. Pat. No. 4,917,994; on a support with reduced oxygen permeability (EP 553,339); with epoxy solvents (EP 164,961); with nickel complex stabilizers (U.S. Pat. Nos. 4,346,165; 4,540,653 and 4,906,559 for example); with ballasted chelating agents such as those in U.S. Pat. No. 4,994,359 to reduce sensitivity to polyvalent cations such as calcium; and with stain reducing compounds such as described in U.S. Pat. No. 5,068,171. Other compounds useful in combination with the invention are disclosed in Japanese Published Applications described in Derwent Abstracts having accession numbers as follows: 90-072,629, 90-072,630; 90-072,631; 90-072,632; 90-072,633; 90-072,634; 90-077,822; 90-078,229; 90-078,230; 90-079,336; 90-079,337; 90-079,338; 90-079,690; 90-079,691; 90-080,487; 90-080,488; 90-080,489; 90-080,490; 90-080,491; 90-080,492; 90-080,494; 90-085,928; 90-086,669; 90-086,670; 90-087,360; 90-087,361; 90-087,362; 90-087,363; 90-087,364; 90-088,097; 90-093,662; 90-093,663; 90-093,664; 90-093,665; 90-093,666; 90-093,668; 90-094,055; 90-094,056; 90-103,409; 83-62,586; 83-09,959.

Especially useful in this invention are tabular grain silver halide emulsions. Specifically contemplated tabular grain emulsions are those in which greater than 50 percent of the total projected area of the emulsion grains are accounted for by tabular grains having a thickness of less than 0.3 micron (0.5 micron for blue sensitive emulsion) and an average tabularity (T) of greater than 25 (preferably greater than 100), where the term "tabularity" is employed in its art recognized usage as $$T=ECD/t^2$$

where

ECD is the average equivalent circular diameter of the tabular grains in micrometers and t is the average thickness in micrometers of the tabular grains.

The average useful ECD of photographic emulsions can range up to about 10 micrometers, although in practice emulsion ECD's seldom exceed about 4 micrometers. Since both photographic speed and granularity increase with increasing ECD's, it is generally preferred to employ the smallest tabular grain ECD's compatible with achieving aim speed requirements.

Emulsion tabularity increases markedly with reductions in tabular grain thickness. It is generally preferred that aim tabular grain projected areas be satisfied by thin (t<0.2 micrometer) tabular grains. To achieve the lowest levels of granularity it is preferred that aim tabular grain projected areas be satisfied with ultrathin (t<0.06 micrometer) tabular grains. Tabular grain thicknesses typically range down to about 0.02 micrometer. However, still lower tabular grain thicknesses are contemplated. For example, Daubendiek et al U.S. Pat. No. 4,672,027 reports a 3 mole percent iodide tabular grain silver bromoiodide emulsion having a grain thickness of 0.017 micrometer. Ultrathin tabular grain high chloride emulsions are disclosed by Maskasky U.S. Pat. No. 5,217,858.

As noted above tabular grains of less than the specified thickness account for at least 50 percent of the total grain projected area of the emulsion. To maximize the advantages of high tabularity it is generally preferred that tabular grains satisfying the stated thickness criterion account for the highest conveniently attainable percentage of the total grain projected area of the emulsion. For example, in preferred emulsions, tabular grains satisfying the stated thickness criteria above account for at least 70 percent of the total grain projected area. In the highest performance tabular grain emulsions, tabular grains satisfying the thickness criteria above account for at least 90 percent of total grain projected area.

Suitable tabular grain emulsions can be selected from among a variety of conventional teachings, such as those of the following: Research Disclosure, Item 22534, January 1983, published by Kenneth Mason Publications, Ltd., Emsworth, Hampshire P010 7DD, England; U.S. Pat. Nos. 4,439,520; 4,414,310; 4,433,048; 4,643,966; 4,647,528; 4,665,012; 4,672,027; 4,678,745; 4,693,964; 4,713,320; 4,722,886; 4,755,456; 4,775,617; 4,797,354; 4,801,522; 4,806,461; 4,835,095; 4,853,322; 4,914,014; 4,962,015; 4,985,350; 5,061,069 and 5,061,616.

The emulsions can be surface-sensitive emulsions, i.e., emulsions that form latent images primarily on the surfaces of the silver halide grains, or the emulsions can form internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent.

Photographic elements can be exposed to actinic radiation, typically in the visible region of the spectrum, to form a latent image and can then be processed to form a visible dye image. Processing to form a visible dye image includes the step of contacting the element with a color developing agent to reduce developable silver halide and oxidize the color developing agent. Oxidized color developing agent in turn reacts with the coupler to yield a dye.

With negative-working silver halide, the processing step described above provides a negative image. The described elements can be processed in the known Kodak C-41 color process as described in The British Journal of Photography Annual of 1988, pages 191–198. Where applicable, the element may be processed in accordance with color print processes such as the RA-4 process of Eastman Kodak Company as described in the British Journal of Photography Annual of 1988, Pp 198–199. Such negative working emulsions are typically sold with instructions to process using a color negative method such as the mentioned C-41 or RA-4 process. To provide a positive (or reversal) image, the color development step can be preceded by development with a non-chromogenic developing agent to develop exposed silver halide, but not form dye, and followed by uniformly fogging the element to render unexposed silver halide developable. Such reversal emulsions are typically sold with instructions to process using a color reversal process such as E-6. Alternatively, a direct positive emulsion can be employed to obtain a positive image.

Preferred color developing agents are p-phenylenediamines such as:

4-amino-N,N-diethylaniline hydrochloride, 4-amino-3-methyl-N,N-diethylaniline hydrochloride, 4-amino-3-methyl-N-ethyl-N-(2-methanesulfonamidoethyl)aniline sesquisulfate hydrate, 4-amino-3-methyl-N-ethyl-N-(2-hydroxyethyl)aniline sulfate, 4-amino-3-(2-methanesulfonamido-ethyl)-N,N-diethylaniline hydrochloride and 4-amino-N-ethyl-N-(2-methoxyethyl)-m-toluidine di-p-toluene sulfonic acid.

Development is usually followed by the conventional steps of bleaching, fixing, or bleach-fixing, to remove silver or silver halide, washing, and drying.

Couplers of the invention may be prepared in accordance with the following scheme:

Synthetic Scheme
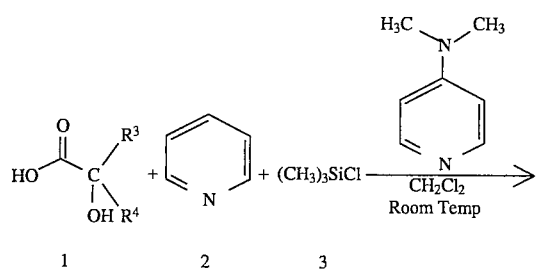
1   2   3
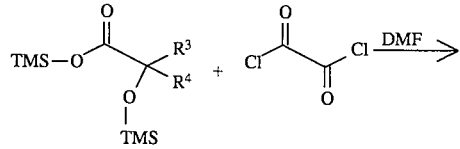
TMS = trimethylsilane
4
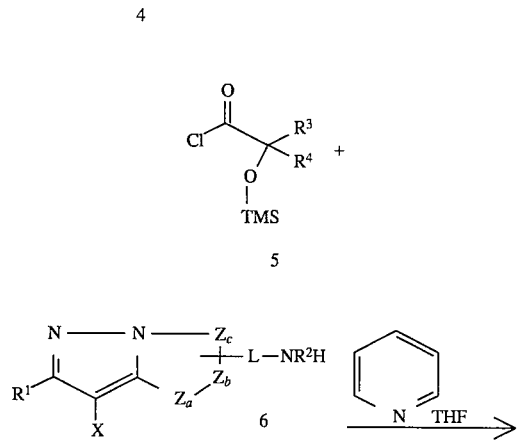
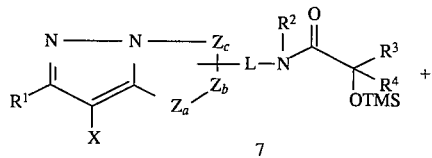
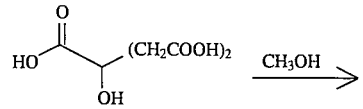
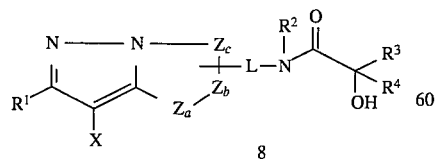
SYNTHETIC EXAMPLE
Synthesis of Coupler M-1
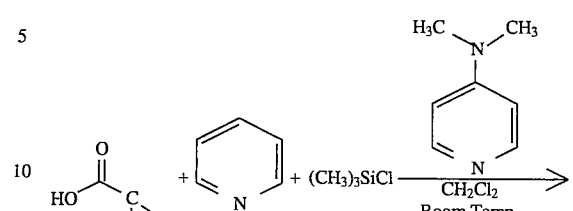
9   2   3
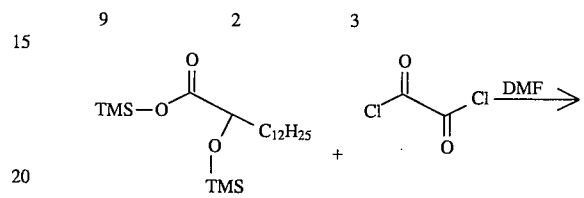
TMS = trimethylsilane
10
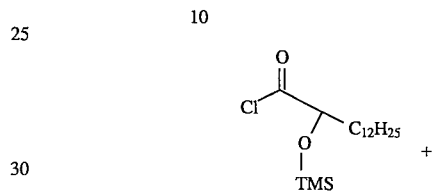
11
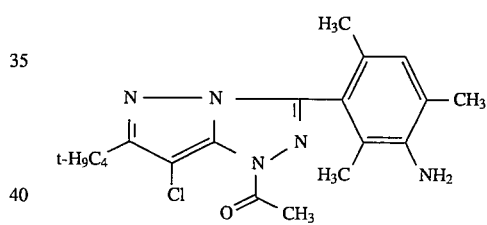
12
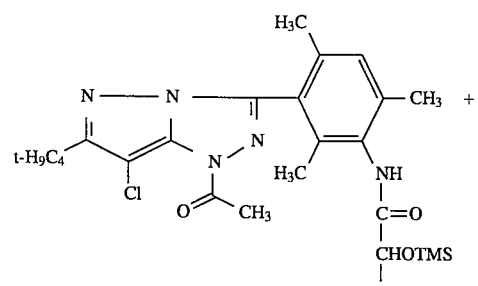
13
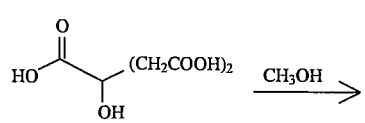

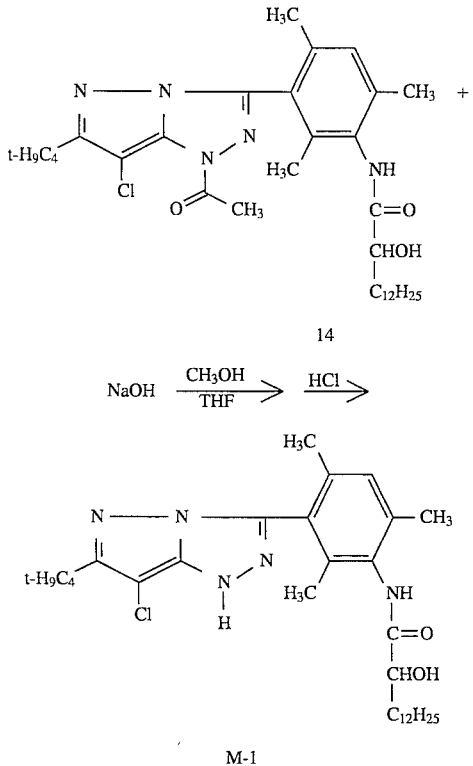

(A) Preparation of Reagent 11

A mixture of 5.37 g (22 mmol) of 2-hydroxy-tetradecanoic acid 9, 0.02 g of DMAP, 3.68 mL (46 mmol) of pyridine in 58 mL of $CH_2Cl_2$ at room temperature was added slowly, via an addition funnel, 5.85 mL (46 mmol) of trimethylchlorosilane 3. A mild exotherm was observed. After the addition, the reaction had been stirred for 4 h at room temperature. To the resulting slurry cooled to 0° C. was added 4 drops of DMF followed by the slow addition of 1.93 mL (22.7 mmol) of oxalyl chloride. During the addition, the reaction temperature was kept below 10° C. After the addition, the reaction was further stirred at 0°–5° C. for 1 h and at 20° C. for ½ h.

(B) Preparation of 1-acetyl-6-tert-butyl-3-(3-(2-hydroxytetradecanamido)-2,4,6-trimethylphenyl)pyrazolo[3,2-c][1,2,4]triazole 14

To the reaction mixture containing the reagent 11 cooled to 0° C., was slowly added 7.47 g (20 mmol) of 1-acetyl-6-tert-butyl-3-[3-amino-2,4,6-trimethylphenyl)-pyrazolo[3,2-c][1,2,4]triazole 12 in 20 mL of pyridine and in 20 mL of THF. The reaction temperature was kept below 10° C. After the addition had been completed, the reaction was further stirred at 20° C. for 2 h. The reaction was completed as evidenced by the TLC analysis (solvent: $CH_3OAc/CH_2Cl_2=1/1$) showing the complete absence of 12. To the above reaction mixture was added at room temperature a solution of 3.84 g (20 mmol) of citric acid in 35 mL of $CH_3OH$. After the addition, the reaction was stirred overnight at 30° C. To the reaction mixture was added with stirring 175 mL of ethyl acetate, followed by the addition of 260 mL of 1N aqueous solution of HCl. The mixture was stirred at room temperature for ½ h. The pH of the mixture was verified to be at about 1. The layers were separated. The aqueous layer was extracted with 175 mL of $CH_3CO_2C_2H_5$. The combined organic extracts were washed with a saturated aqueous solution of sodium bicarbonate, followed by the wash with brine. The organic phase was dried over $MgSO_4$ and concentrated to yield 9.82 g (81.80%) of the desired product 14. All the analytical data confirmed the assigned structure.

(C) Preparation of the Coupler (M-1): 1-H-6-tert-butyl-3-(3-(2-hydroxy-tetradecanamido-2,4,6-trimethylphenyl)-pyrazolo[3,2-c][1,2,4]triazole To a solution of 9.82 g (16.36 mmol) of 14 in a mixture of solvents $CH_3OH/THF$: 10 mL/10 mL was added 1.24 mL of 50% w/w NaOH. The mixture was heated to 50° C. and kept at 50° C. for 1 h. The reaction was completed as evidenced by the TLC analysis (solution system:AcOEt/$CH_2Cl_2=1/1$). The cooled mixture was partitioned between 500 mL of ethyl acetate and 120 mL of water. The layers were separated and the aqueous layer was extracted with ethyl acetate. The combined organic extracts were washed with brine, dried over $MgSO_4$ and concentrated in vacuo to yield 9.65 g of crude coupler. It was purified by slurrying in warm acetonitrile to yield 6.84 g (75%) of pure coupler M-1. All analytical data confirmed the assigned structure.

Photographic Examples

On a gel-subbed, polyethylene-coated paper support were coated the following layers:

First Layer

An underlayer containing 3.23 grams gelatin per square meter.

Second Layer

A photosensitive layer containing (per square meter) 1.61 grams gelatin, 0.17 gram green-sensitized silver chloride emulsion (expressed as silver), a dispersion containing $4.74 \times 10^{-4}$ mole of coupler, and 0.043 gram surfactant Alkanol XC (trademark of E. I. Dupont Co.)(in addition to the Alkanol XC used to prepare the coupler dispersion). The coupler dispersion contained the coupler, all of the gelatin in the layer except that supplied by the emulsion, an amount of coupler solvent (SOL), and an amount of stabilizer (S) as indicated below and Alkanol XC equal to the weight of gelatin in the dispersion multiplied by 0.1.

For the solvents, SOL-1=dibutyl phthalate; SOL-2=didecyl phthalate and SOL-3=tri-2-ethylhexyl phosphate, and SOL-4=tritolylphosphate.

For the samples in the indicated tables, the weight ratio of dispersion components was as indicated:

Tables II and III
  Coupler/SOL-1/SOL-2/S-1/S-2=1/1/1/0.5/0.5.
Table IV
  Coupler/SO-3/S-3=1/2.5/0.5
Tables V, VI, and VII
  Coupler/SO-4/S-3=1/2.5/0.5.

Third Layer

An ultraviolet-absorbing layer containing (per square meter) 1.33 grams gelatin, 0.73 grams 2-(2H-benzotriazol-2-yl)-4,6-bis(1,1-dimethylpropyl)phenol, 0.13 gram Tinuvin 326 (trademark of Ciba-Geigy), and 0.043 gram Alkanol XC.

Fourth Layer

A protective layer containing (per square meter) 1.40 grams gelatin, 0.14 gram bis(vinylsulfonyl)methane, 0.043 gram Alkanol XC, and $4.40 \times 10^{-6}$ gram tetraethylammonium perfluorooctanesulfonate.

Stabilizers employed were:

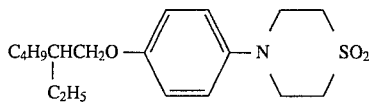

S-1

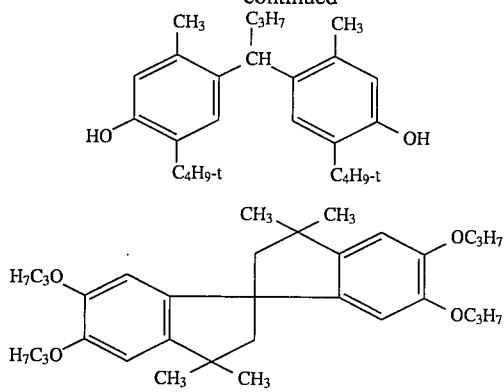

S-2

S-3

Processed samples were prepared by exposing the coatings through a step wedge and processing as follows:

| Process Step | Time (min.) | Temp. (C.) |
|---|---|---|
| Developer | 0.75 | 35.0 |
| Bleach-Fix | 0.75 | 35.0 |
| Water Wash | 1.50 | 35.0 |

The processing solutions used in the above process had the following compositions (amounts per liter of solution):

| Developer | |
|---|---|
| Triethanolamine | 12.41 g |
| Blankophor REU (trademark of Mobay Corp.) | 2.30 g |
| Lithium polystyrene sulfonate | 0.09 g |
| N,N-Diethylhydroxylamine | 4.59 g |
| Lithium sulfate | 2.70 g |
| N-{2-[4-amino-3-methylphenyl)ethylamino]-ethyl}methanesulfonamide, sesquisulfate | 5.00 g |
| 1-Hydroxyethyl-1,1-diphosphonic acid | 0.49 g |
| Potassium carbonate, anhydrous | 21.16 g |
| Potassium chloride | 1.60 g |
| Potassium bromide | 7.00 mg |
| pH adjusted to 10.4 at 26.7C | |

| Bleach-Fix | |
|---|---|
| Solution of ammonium thiosulfate | 71.85 g |
| Ammonium sulfite | 5.10 g |
| Sodium metabisulfite | 10.10 g |
| Acetic acid | 10.20 g |
| Ammonium ferric ethylenediaminetetraacetate | 48.58 g |
| Ethylenediaminetetraacetic acid | 3.86 g |
| pH adjusted to 6.7 at 26.7C | |

The samples were tested to determine whether the improvements. in photographic performance, especially in image dye light stability, are indeed due to the combination of substituents.

The samples were subjected stepwise to a green light exposure in the conventional manner. The reflection density to green light of each step of the processed strip was read. From the resulting densities, the following parameters are calculated:

Dmax (maximum density): The highest density measured.

Dmin (minimum density): The lowest density measured.

Speed: The relative log exposure required to yield a density of 1.0.

Shoulder Density: The density produced at a log exposure 0.3 units greater than the speed point as defined above.

Toe density: The density produced by a log exposure 0.3 units less than the speed point as defined above.

Contrast: The slope of a straight line connecting the shoulder and toe density points as defined above.

Density Loss: The initial density of a test strip is measured and compared to the dye density remaining after the strip is subjected to irradiation by light of a xenon arc lamp at an intensity of 50 klux or 5.4 klux for the indicated period of time. The loss in density, from the indicated density level, expressed as a % or as units of density loss, is reported.

The following comparison couplers were tested.

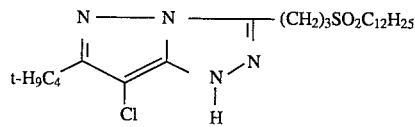

C-1

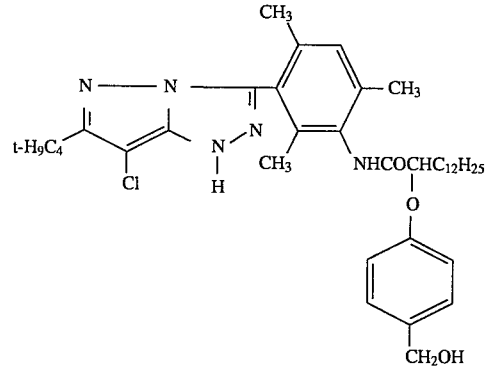

C-2

C-3
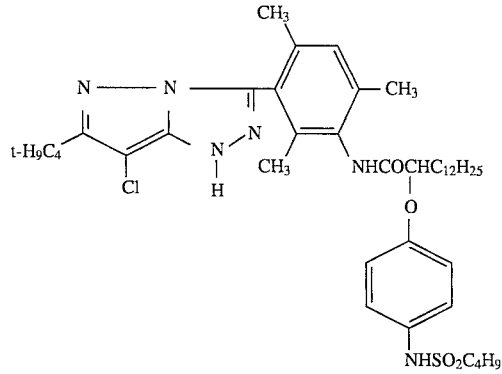
C-4
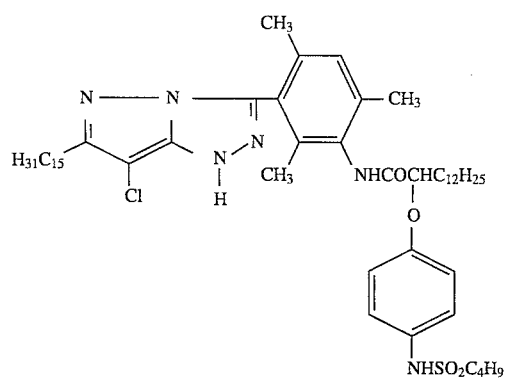
C-5
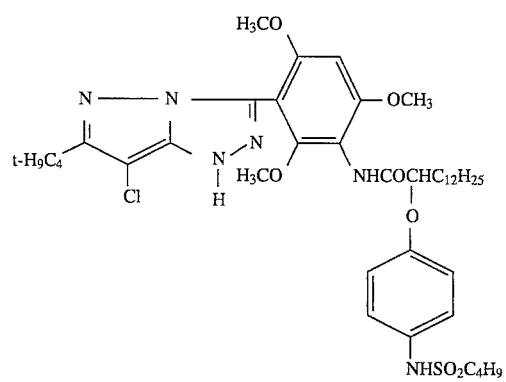
C-6
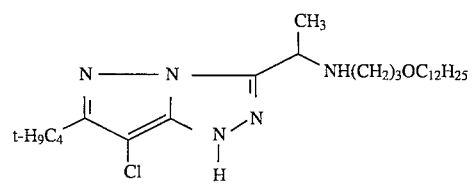

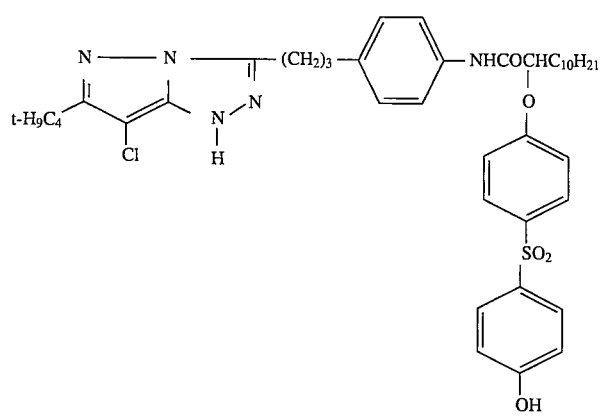
C-7
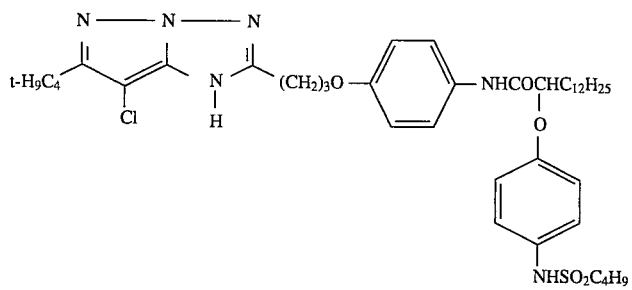
C-8
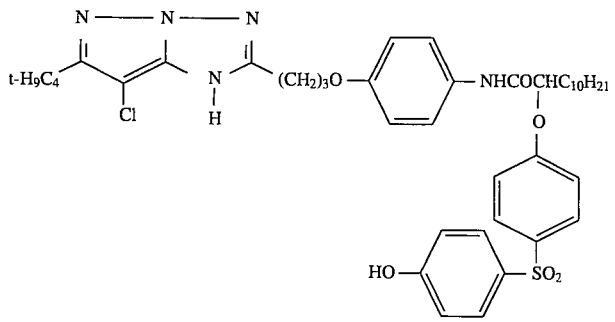
C-9
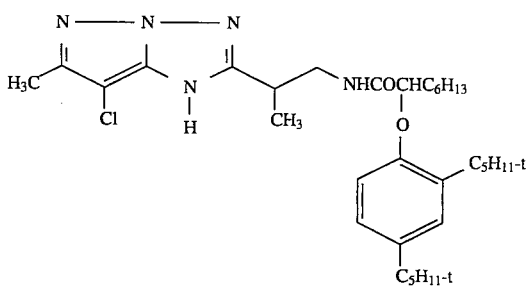
C-10
| | TABLE I | | | |
|---|---|---|---|---|
| | SAMPLE TYPES | | | |
| | | WITHIN INVENTION? Yes (Y) or No (N) | | |
| | | | 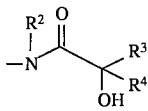 | |
| COUPLER | TYPE | $R^1$ | $R^2$ | $R^3$, $R^4$, OH |
| M-1 | Inv | Y | Y | |
| M-2 | Inv | Y | Y | |
| | TABLE I-continued | | | |
|---|---|---|---|---|
| | SAMPLE TYPES | | | |
| | | WITHIN INVENTION? Yes (Y) or No (N) | | |
| | | | 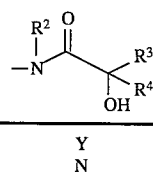 | |
| COUPLER | TYPE | $R^1$ | $R^2$ $R^3$, $R^4$, OH | |
| M-3 | Inv | Y | Y | |
| C-1 | Comp | Y | N | |

TABLE I-continued

SAMPLE TYPES

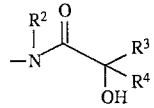

| COUPLER | TYPE | R¹ | WITHIN INVENTION? Yes (Y) or No (N) |
|---|---|---|---|
| C-2 | Comp | Y | N |
| C-3 | Comp | Y | N |
| C-4 | Comp | N | N |
| C-5 | Comp | Y | N |
| C-6 | Comp | Y | N |
| C-7 | Comp | Y | N |
| C-8 | Comp | Y | N |
| C-9 | Comp | Y | N |
| C-10 | Comp | N | N |

TABLE II

RESULTS OF TESTING

| | | Density Loss From Original | | | | | |
|---|---|---|---|---|---|---|---|
| | | 6 week 5.4 klux daylight | | | 12 week 5.4 klux daylight | | |
| Coupler | Type | 0.5 | 1.0 | 1.7 | 0.5 | 1.0 | 1.7 |
| M-1 | Inv. | −0.01 | 0.00 | −0.01 | −0.07 | −0.09 | −0.13 |
| C-1 | Comp. | −0.04 | −0.07 | −0.14 | −0.15 | −0.21 | −0.36 |
| C-2 | Comp. | −0.03 | −0.05 | −0.08 | −0.09 | −0.13 | −0.19 |
| C-3 | Comp. | −0.03 | −0.07 | −0.12 | −0.09 | −0.14 | −0.23 |
| C-4 | Comp. | −0.07 | −0.08 | −0.14 | −0.20 | −0.25 | −0.36 |
| C-5 | Comp. | −0.04 | −0.04 | −0.11 | −0.12 | −0.15 | −0.26 |

TABLE III

RESULTS OF TESTING

| | | Density Loss From Original | | | |
|---|---|---|---|---|---|
| | | 2 week 50 klux daylight | | 12 week 5.4 klux daylight | |
| Couplers | Type | 1.00 | 1.70 | 1.00 | 1.70 |
| M-1 | Inv. | −0.25 | −0.35 | −0.09 | −0.13 |
| C-1 | Comp. | −0.27 | −0.41 | −0.15 | −0.27 |
| C-4 | Comp. | −0.51 | −0.71 | −0.25 | −0.36 |
| C-5 | Comp. | −0.31 | −0.49 | −0.15 | −0.26 |

TABLE IV

RESULTS OF TESTING

| | | Density Loss From Original | | | |
|---|---|---|---|---|---|
| | | 2 week 50 klux daylight | | 24 week 5.4 klux daylight | |
| Couplers | Type | 1.0 | 1.7 | 1.0 | 1.7 |
| M-2 | Inv. | −0.63 | −0.84 | −0.84 | −1.08 |
| C-1 | Comp. | −0.79 | −1.12 | −0.89 | −1.44 |
| C-6 | Comp. | −0.90 | −1.14 | −0.91 | −1.53 |
| C-7 | Comp. | −0.81 | −1.47 | −0.86 | −1.53 |

TABLE V

RESULTS OF TESTING

| | | Density Loss From Original | | | | | |
|---|---|---|---|---|---|---|---|
| | | 2 week 50 klux daylight | | | 4 week 50 klux daylight | | |
| Coupler | Type | 0.5 | 1.0 | 1.7 | 0.5 | 1.0 | 1.7 |
| M-3 | Inv. | −0.01 | 0.03 | −0.04 | −0.05 | −0.08 | −0.14 |
| C-8 | Comp. | −0.021 | −0.03 | −0.08 | −0.06 | −0.09 | −0.15 |
| C-9 | Comp. | −0.01 | −0.03 | −0.06 | −0.05 | −0.09 | −0.14 |
| C-10 | Comp. | −0.05 | −0.09 | −0.16 | −0.13 | −0.21 | −0.31 |

TABLE VI

RESULTS OF TESTING

| Coupler | Type | Density Loss From Original 24 week 5.4 klux at 1.7 |
|---|---|---|
| M-3 | Inv | −0.08 |
| C-8 | Comp | −0.09 |
| C-9 | Comp | −0.13 |
| C-10 | Comp | −0.21 |

TABLE VII

RESULTS OF TESTING

| Coupler | Type | Density Loss From Original 2 week, 50 klux sunshine | | |
|---|---|---|---|---|
| | | 0.5 | 1.0 | 1.7 |
| M-3 | Inv. | −0.02 | −0.05 | −0.05 |
| C-8 | Comp. | −0.04 | −0.05 | −0.07 |
| C-9 | Comp. | −0.03 | −0.05 | −0.06 |
| C-10 | Comp. | −0.05 | −0.09 | −0.16 |

Tables II through VII provide the results of testing separately prepared groups of samples. The results of Table II show that without the specified hydroxy substituent on the carbon alpha to the acyl carbon, the desired light stability is not obtained. The comparisons either contain no nitrogen in the substituent (C-1), contain no hydroxy group (C-3, C-4, C-5), or contain the hydroxy group in the wrong location (C-2). Table III shows a similar result.

Table IV uses a different inventive coupler and a slightly altered sample format but the same relative results are apparent. M-2 differs from M-1 in that there is a nitrogen substituent on the M-2 molecule.

Tables V, VI, and VII compare a third inventive coupler, M-3, with comparatives C-8, C-9, and C-10 under various lighting conditions. Here the inventive coupler contains a long linking group L to the nitrogen atom. The comparisons C-8 and C-9 contain a similar long linking group but do not contain the hydroxy group on the carbon alpha to the nitrogen atom as specified in the invention. C-10 contains a shorter linking group and has a common ballast group substituent. Again, the inventive coupler provides superior results vs the comparisons.

The entire contents of the various copending applications as well as patents and other publications cited in this specification are incorporated herein by reference.

What is claimed is:

1. A photographic light sensitive silver halide emulsion layer having associated therewith a pyrazoloazole dye-forming coupler having the formula:

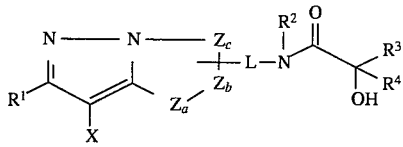

wherein:

$R^1$ is a substituent bonded to the pyrazolotriazole nucleus by a fully substituted carbon atom;

X is hydrogen or a coupling-off group;

L is a divalent linking group;

$R^2$, $R^3$, and $R^4$ are independently hydrogen or substituent groups; and $Z_a$, $Z_b$, and $Z_c$ are independently —C(R')(R")—, =N—, =C(R')—, or —NH—, wherein R', and R" are independently H or a substituent, provided that one of either the $Z_a$—$Z_b$ or the $Z_b$—$Z_c$ bond is a double bond and the other is a single bond, and provided that when the $Z_b$—$Z_c$ bond is a double bond, it may form part of a fused ring.

2. The layer of claim 1 wherein $R^1$ is selected from tertiary carbon groups containing from 4 to 8 carbon atoms.

3. The layer of claim 2 wherein $R^1$ is selected from the group consisting of t-butyl, t-pentyl, and a methyl-diethyl methyl group.

4. The layer of claim 1 wherein X is a coupling-off group.

5. The layer of claim 1 wherein the coupling-off group is selected from the group consisting of aryloxy, arylthio, halogen, and nitrogen heterocyclic groups.

6. The layer of claim 5 wherein the coupling-off group is chloride or a nitrogen containing heterocyclic group.

7. The layer of claim 6 wherein the nitrogen heterocycle is a group of the formula:

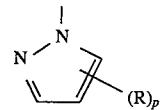

wherein each R is an independently selected substituent and p is 0 to 3.

8. The layer of claim 6 wherein X is chloride, $R_2$ is hydrogen, and $R_3$ and $R_4$ are independently selected from the group consisting of hydrogen and alkyl or alkoxy groups of 1 to 16 carbon atoms and aryl or aryloxy groups of up to 48 carbon atoms.

9. The layer of claim 1 wherein $R^4$ is selected from the group consisting of alkyl, alkoxy, aryl and aryloxy groups and $R^2$ and $R^3$ are independently selected from hydrogen and the groups from which $R^4$ may be selected.

10. The layer of claim 9 wherein $R^2$ comprises groups selected from alkyl and aryl groups, such groups separated by an oxygen atom.

11. The layer of claim 9 wherein $R^2$ is hydrogen.

12. The layer of claim 9 wherein $R^2$ and $R^3$ are independently selected from the group consisting of hydrogen, alkyl, and phenyl groups.

13. The layer of claim 9 wherein $R^2$, $R^3$, and $R^4$ are independently selected from the group consisting of hydrogen, alkyl groups of 1 to 16 carbon atoms and phenyl groups.

14. The layer of claim 1 wherein L contains a divalent alkylene or arylene group.

15. The layer of claim 14 wherein L contains two or more alkylene or arylene groups interrupted by an oxygen atom.

16. The layer of claim 1 wherein $Z_a$ is —NH—, $Z_b$ is =N—, and $Z_c$ is =C(R')—.

17. The layer of claim 1 wherein $Z_a$ is —NH—, $Z_b$ is =C(R')—, and $Z_c$ is =N—.

18. A photographic element comprising an emulsion layer of claim 1.

19. The element of claim 18 wherein the nature, number and size of the substituent groups $R^1$ through $R^4$ are sufficient to render the coupler nondiffusible during aqueous alkaline development processing of the element.

20. A photographic element comprising an emulsion layer of claim 8.

21. A method of forming an image in an element as described in claim 18 after the element has been imagewise exposed to light, comprising contacting the element with a color developing agent.

22. A method of forming an image in an element as described in claim 18 after the element has been imagewise exposed to light, comprising contacting the element with a color developing agent.

* * * * *